United States Patent [19]

Poynton et al.

[11] Patent Number: 4,920,061
[45] Date of Patent: Apr. 24, 1990

[54] BIOLOGICAL MAGNETIC COLLOIDS

[75] Inventors: Christopher H. Poynton, London, England; Christopher L. Reading, Kingwood, Tex.

[73] Assignee: The University of Texas System, Austin, Tex.

[21] Appl. No.: 883,359

[22] Filed: Jul. 8, 1986

Related U.S. Application Data

[63] Continuation-in-part of Ser. No. 585,888, Mar. 2, 1984, abandoned.

[51] Int. Cl.$^5$ ............... G01N 33/553; G01N 33/543; B01F 3/00
[52] U.S. Cl. .................... 436/526; 436/518; 436/524; 436/525; 252/302
[58] Field of Search ............... 436/526, 548, 518, 525; 252/302, 303, 304, 310, 315.2, 254; 420/435; 435/174, 176, 29, 7

[56] References Cited

U.S. PATENT DOCUMENTS

| | | | |
|---|---|---|---|
| Re. 29,474 | 11/1977 | Axen et al. | 424/1 |
| 3,796,634 | 3/1974 | Haynes | 195/63 |
| 3,970,518 | 7/1976 | Giaever | 195/1.5 |
| 4,096,316 | 6/1978 | Tamai et al. | 252/62.54 |
| 4,115,534 | 9/1978 | Ithakissios | 424/1 |
| 4,158,547 | 6/1979 | Rousseau et al. | 23/230.6 |
| 4,219,335 | 8/1980 | Ebersole | 23/230 |
| 4,228,237 | 10/1980 | Hevey et al. | 435/7 |
| 4,267,234 | 5/1981 | Rembaum | 428/403 |
| 4,335,094 | 6/1982 | Mosbach | 424/1 |
| 4,452,773 | 6/1984 | Molday | 424/1.1 |
| 4,454,234 | 6/1984 | Czerlinski | 436/526 |
| 4,477,576 | 10/1984 | Deutsch et al. | 436/500 |
| 4,550,086 | 10/1985 | Reinherz et al. | 436/548 |
| 4,582,810 | 4/1986 | Rosenstein | 436/548 |
| 4,687,748 | 8/1987 | Schröder | 435/7 |
| 4,735,796 | 4/1988 | Gordon | 424/86 |

FOREIGN PATENT DOCUMENTS

| | | |
|---|---|---|
| 2334106 | 7/1977 | France. |
| 2463807 | 2/1981 | France. |
| 2152664 | 8/1985 | United Kingdom. |
| 8300106 | 10/1983 | World Int. Prop. O.. |

OTHER PUBLICATIONS

"Receptor Affinity Chromatography Based on the Avidin-Biotin Interaction", *Biotin*, Annals of the New York Academy of Sciences, New York, N.Y., (1985), vol. 447, pp. 359-372.

Avrameas, et al., *Coupling of Enzymes to Antibodies and Antigens*, 8 Scand. J. Immunol., Suppl. 7, 7-23, (1978).

Chard, *An Introduction to Radioaminoassay and Related Techniques*, Elsevier Biomedical Press, (1982).

Massart, *Preparation of Aqueous Magnetic Liquids and Alkaline and Acidic Media*, IEEE Transactions on Magnetics, vol. Mg.-17, No. 2, Mar. 1981.

Popplewell, et al., *Magnetic Liquids—The New Technology*, New Scientist, Sep. 25, 1980.

Poynton, et al., *Immunomagnetic Removal of Calla Positive Cells From Human Bone Marrow*, The Lancet, Mar. 5, 1983.

Poynton, et al., *Monoclonal Antibodies: The Possibilities for Cancer Therapy*, Experimental Biology, vol. 43, pp. 13-33, (1984).

Reading, *Procedures for In-Vitro Immunization and Monoclonal Antibody Production*, Proceedings of the Second Houston Symposium, "Hybrodomas and Cellular Immortality", (B. Tom and J. Allison, Eds. 1983, Plenum Press, N.Y.).

Schwoch, et al., *Preparation and Properties of Human Erythrocyte Ghosts*, Molecular and Cellular Biochemistry, vol. 2, No. 2, Dec. 15, 1973.

Dicke, et al., *Elimination of Leukemic Cells from Remission Marrow Suspensions by an Immunomagnetic Procedure*, Proceedings for the International Symposium on the Detection and Treatment of Minimal Residual Disease, in Acute Leukemia, (1984), pp. 209-221.

*Primary Examiner*—Robert J. Warden
*Assistant Examiner*—Janelle Grater
*Attorney, Agent, or Firm*—Arnold, White & Durkee

[57] ABSTRACT

Colloidal-sized paramagnetic particles are formed with affinity ligands directly adsorbed to their surface. The colloidal-sized particles can form a colloidal disperse phase which is distributed through an aqueous dispersion medium to form a biological magnetic fluid. The fluid can be used to selectively separate cells from a cell mixture.

15 Claims, No Drawings

BIOLOGICAL MAGNETIC COLLOIDS

BACKGROUND OF THE INVENTION

This is a continuation-in-part of U.S. Pat. Application Ser. No. 585,888 filed Mar. 2, 1984, now abandoned.

The invention relates generally to magnetic colloidal liquids useful for biological and medical applications. More particularly, the invention is directed to novel colloidal-sized paramagnetic particles coated with biologically active molecules or affinity ligands. The particles are useful, for example, in allogenic bone marrow transplantation for the prevention of graft versus host disease, in autologous bone marrow transplantation, for the elimination of residual tumor cells, and for the separation of specific cell populations from cell mixtures in general.

The combination of high dose chemotherapy and total body irradiation followed by bone marrow infusion from an identical sibling compatible donor has been developed over the last ten years for the management of malignant hemopoietic disorders. This method is effective in the treatment of relapsed leukemia and has led to a 15 to 20 percent two year disease free survival rate.

The main stumbling block of allogenic bone marrow transplantation is the acute graft-versus-host reaction. One of the main inducing factors of acute graft-versus-host reaction is the infused lymphoid cells, which are present in the bone marrow graft. In spite of donor-recipient major histocompatibility locus (or complex) identity, the frequency of clinical manifestation of donor-versus-host reactions is 50 percent. In approximately 25 percent of the cases, the manifestation is lethal.

When a compatible bone marrow donor is not available, autologous transplantation can be performed. In this case, marrow is aspirated from patients in remission and cryopreserved. After the patient is treated with high dose chemotherapy to eliminate residual cancer cells, the marrow is thawed and reinfused to rescue the hematopoietic system which is eliminated by the high dose chemotherapy. This procedure is complicated by the fact that residual tumor cells may be present in the stored marrow. These cells may cause recurrence of disease after infusing the marrow.

The advent of monoclonal antibodies has opened a new frontier for the characterization of cell surface antigens. By immunizing mice, removing the immune spleen cells and hybridizing them with mouse myelomas, many groups have produced cloned antibody producing tumor cells (hybridomas) of predefined specificity. Each of these separate clones produces an antibody to a single determinant of the immunogen. By analysis of the individual specificities of the hybridomas, polyclonal antibody response can be segregated into specific and nonspecific clones. In this manner, exquisitely specific immunological reagents can be produced. Since the clones, which remain stable for antibody production and for proliferation, can be grown in culture and as ascites tumors in mice indefinitely, a virtually unlimited supply of these reagents can be prepared, and the identical antibodies can be utilized around the world. The potential for transplantation has been realized by many different groups. Monoclonal antibodies which react with the components on the surface of leukemic cells have been reported by several groups, and some groups have used monoclonal antibody treatment of bone marrow prior to transplantation.

Work has started on techniques for linking a monoclonal antibody to a boron containing compound. Diseased tissue, targeted by the antibody, may be exposed to a "slow" (thermal) neutron beam with the hope that significant cell kill could be obtained. When the isotope of boron, $^{10}B$, is exposed to a thermal neutron beam, it decomposes to lithium together with an alpha particle (a helium nucleus), with enough energy to kill cells within a radius of about 10 microns. This technique has been limited because only a few molecules of boron can be attached to a cell with the procedures used.

The idea of physically and selectively removing unwanted cells from a cell suspension has been studied by a large number of investigators. Particularly in the treatment of cancer, the removal of cells circumvents numerous problems involved in using toxins, chemotherapeutic agents and complement but has been limited to in vitro physical removal. Density gradient separations have been used to remove residual cancer cells from bone marrow cells, but these were not highly efficient.

Magnetic liquids generally are known. A widely described magnetic liquid, known as a ferro-fluid, uses magnetite (ferro-ferric oxide) as the colloidal dispersed phase which is distributed through a liquid dispersion medium such as water, paraffin, toluene or indeed any liquid, including mercury. A surfactant material, or wetting agent, such as oleic acid is usually added to the mixture to prevent the particles from aggregating and ultimately forming a sediment The surfactant normally binds to the surfaces of the magnetite particles and keeps them colloidally dispersed in the ferro-fluid. These fluids are not compatible with aqueous or biological systems.

Metallic colloids began to interest biologists in the 1960's, when their property of binding macromolecules particularly proteins almost irreversibly. was discovered. Metallic colloidal gold, the most studied colloidal liquid, is used as a marker, linked to specific carrier proteins for electron microscopy.

Various types of magnetic particles have been used for several years in solid phase immunoassays, drug targeting, and more recently, for cell separations. The magnetic material most often used is magnetite, incorporated into a variety of carrier particles or microspheres with antibody attached. Very regular polymeric spheres can be made and then coated with other polymers by a gamma irradiation technique to allow adsorption of antibody to the surface. While cell separations have been attempted using them, these spheres are not easy to prepare and tend to aggregate during protein coupling. Magnetite-polystyrene spheres have been used for in vitro magnetic cell separations of a neuroblastoma cell line added in various proportions to normal bone marrow. Approximately 97 to 99 percent of the antibody reactive cells could be removed. One problem encountered with magnetic particles of this variety is that they can be pulled off the cell. Further, these are large spheres which cannot be sterilized by filtration and do not stay in suspension. These particles, therefore, depend on direct collisions in order to react with the cells.

Dextran coated magnetite particles have also been prepared by researchers. The colloidal magnetite is formed in the concentrated polysaccharide (dextran) solution. In this way some of the magnetite becomes colloidal, and the rest remains as a sediment. After heat treatment, some of the dextran bonds to the magnetite particles. It is known that antibodies can be coupled covalently to the dextran coated magnetite particles by periodate oxidation methods.

However, it is difficult to produce colloidal particles of magnetite greater than 12 nanometers in diameter. In addition, magnetite particles tend to aggregate, making preparation of a colloid difficult. Moreover, magnetite colloid is not "surface active" in binding proteins. The dextran coating apparently gives the magnetite particles a hydrophilic surface, thereby counteracting the particles tendency to aggregate. However, to attach ligands to the particles to create a useful product generally requires chemical crosslinking. Further, for use in bone marrow transplantation, a greater than 99% removal of cells is desired. To date, a 99% removal of cells has not been possible with dextran-coated magnetite particles.

Although more effective magnetite colloids can be produced, the major problem is one of reproducibility due to the large number of steps involved in producing a useful magnetite colloid. The inconsistency in obtaining a useful magnetite colloid is further compounded by the extended preparation time required to prepare the colloid. For example, depending on the nature of the magnetite preparation, making an effective colloidal magnetite solution generally requires from 2 to 7 days.

SUMMARY OF THE INVENTION

In accordance with one embodiment of the present invention, a biological magnetic fluid includes a magnetic colloidal dispersed phase, distributed throughout a liquid dispersion medium. The dispersed phase includes fine magnetic particles coated with cross-linked biologically compatible polymers.

In accordance with another embodiment of the present invention, a biological magnetic fluid includes a magnetic colloidal dispersed phase distributed throughout a liquid dispersion medium. The dispersed phase includes magnetic particles containing cobalt and a biologically compatible polymer.

In accordance with still another embodiment of the present invention, a method of making a biological magnetic colloid includes the step of forming a biologically incompatible colloid. The biologically incompatible colloid is then slowly added to a biologically compatible polymer.

In accordance with another embodiment of the present invention, a method of making a biological magnetic liquid includes the step of mixing a magnetic metal salt solution with a reducing agent to form a colloid. A low salt biologically compatible polymer is incorporated into the mixture during the formation of the colloid.

One aspect of the present invention is based on the discovery of particular properties of cobalt which make cobalt especially useful for a colloidal affinity separation system for cell mixtures.

Accordingly, in one embodiment, the present invention includes colloidal-sized paramagnetic particles of cobalt coated with affinity ligands. Advantageously, the colloidal-sized particles are at least greater than about 30 nanometers in diameter. The various affinity ligands include avidin, lectins and antibodies. The coated colloidal-sized cobalt particles essentially act as free ligands and react with solution kinetics rather than collision kinetics. These colloidal-sized ligands are capable of binding to a variety of biological molecules under the proper conditions.

In accordance with another embodiment of the present invention, a biological magnetic fluid includes a magnetic colloidal dispersed phase distributed throughout a liquid dispersion medium. The dispersed phase includes magnetic particles of cobalt coated with affinity ligands.

In another embodiment of the present invention, a method of making a magnetic cobalt colloid includes the steps of reducing a suitably complexed cobalt salt solution with a suitable reducing agent to form colloidalsized cobalt particles, and then coating the colloidalsized cobalt particles with affinity ligands. Advantageously, the coated colloidal cobalt can be produced in a relatively short time period, e.g., on the order of about 2 hours rather than over a period of several days. Further, the quality of the cobalt colloid is more consistent since the number of chemical steps involved is reduced.

DETAILED DESCRIPTION AND PREFERRED EMBODIMENTS

A biological magnetic fluid can include a magnetic colloidal dispersed phase distributed throughout a liquid dispersion medium. The magnetic colloidal dispersed phase may be formed of fine particles of magnetite, magnetite coated with cobalt, cobalt, iron or any other paramagnetic metal which possesses sufficiently high paramagnetic properties at the extremely small colloidal particle size to be of use in particular applications. Generally the particles are of a size under 300 nm. for colloid formation. Generally, the greater the particle concentration, the more magnetic the liquid. A suitable low salt biologically compatible polymer, that is, a polymer that is compatible with living cells, is incorporated into the colloid. As used herein, "low salt" means having a salt concentration of less than 10 millimolar. The liquid dispersion medium is preferably an aqueous solution such as a physiological salt solution with a pH of about 7.

The incorporation of the low salt biologically compatible polymer into the colloid can be accomplished either in a one step technique, simultaneously with colloid formation or in a two step technique, subsequent to the formation of an initial colloidal liquid. In the two step technique, a conventional biologically incompatible colloid, which may be toxic, is added to a low salt biologically compatible polymer that can withstand rough treatment. Suitable polymers include biologicals such as albumin, yeast mannan, polymerized sucrose, and dextran, or biologically compatible polymers such as polymethacrylate. The rough treatment that must be sustained and that makes a colloid "biologically incompatible", includes exposure to strong oxidizing and reducing conditions and wide pH variations (as wide as from 3 to 11). It is preferred that the biologically incompatible colloid be slowly added to the biologically compatible polymer, not vice versa, and the rate of addition should be slow enough to avoid visually perceptible aggregation. In the one step technique, the colloid is grown directly in the biological material.

The two step technique for incorporating the biologically compatible polymer can be accomplished using a variety of magnetic materials. Magnetite is advantageous because it is strongly magnetic. A biologically incompatible colloid of magnetite particles or nuclei may be prepared using conventional techniques, for example, as described in the article by R. Massart, "Preparation of Aqueous Magnetic Liquids in Alkaline and Acidic Media", IEEE Transactions in Magnetism, V. 17, No. 2, pp. 1247-1248, March 1981, hereby expressly incorporated herein by reference.

Specifically, an aqueous mixture of ferric chloride and ferrous chloride is added to an ammonia solution. The gelatinous precipitate is isolated from the solution by centrifugation or magnetic decantation without washing with water. An alkaline sol may be formed by peptizing the precipitate with a source of highly charged cations, such as aqueous tetramethyl ammonium hydroxide. While an acidic sol is also possible, an alkaline sol is believed to be highly advantageous for most anticipated applications of the present invention. A sol can only be obtained if the Fe (III)/Fe (II) weight ratio is larger than 2, as it is in $Fe_3O_4$. A suitable low salt biologically compatible polymer may be made by dialyzing versus water. The magnetite fluid is slowly added to the relatively vigorous low salt biologically compatible polymer, such as human albumin, until the pH of the albumin is about 9.5. The concentration of the low salt biologically compatible polymer is at least 10 mg./ml. and preferably at least 30 mg./ml. The solution is centrifuged to remove aggregated material after sitting for a sufficient time, and then filtered.

By adding the biologically compatible polymer before the formation of the biological colloid, better binding of the biologically compatible polymer is achieved because greater stabilization of the colloid may be obtained. In fact, it has been found that the biologically compatible polymer often aids in the process of forming the colloid. It may be desirable to form the ultimate colloid in stages. In the first stage, a preliminary colloidal liquid is prepared, and added to biologically compatible polymer. In the second stage, the growth of the colloidal particles is continued, with the biologically compatible polymer contained on the surface of the colloidal particles.

Magnetic cobalt colloids can be formed through the chemical reduction of cobalt (II) chloride with sodium borohydride ($NaBH_4$). Some of the reaction product is undoubtedly the borides $Co_2B$ and $CoB$, which are also paramagnetic. The same reaction applies to the reduction of iron (II) and (III) chloride, with greater formation of metallic iron rather than iron borides. The formation of the cobalt colloid may be achieved by using either the one step or the two step technique discussed above.

In a preferred embodiment of making magnetic particles, it is desirable to first reduce the salt solution in two stages with a suitable reducing agent. In fact, it has been found that two applications of the salt solution to the reducing agent is highly advantageous. More applications may result in the ability to vary particle sizes. In addition, it is desirable to regulate or retard the rate of the reduction reaction by incorporating a suitable complexing agent. Suitable agents include the organic acids, such as sodium citrate, sodium succinate, sodium tartrate, ethylaminediaminetetracetic acid (EDTA) and the like.

The formation of a colloid with a uniform particle size is important in obtaining a good colloidal suspension. Uniform particle size may be obtained by using a two step reaction process. In a preferred embodiment the particle size ranges from about 30 nanometers to about 60 nanometers. After a first nucleation reaction, additional magnetic material can be grown on the nuclei. It is the number of nuclei first formed that determines the particle size of the colloid, given a finite amount of reactants. Hence, it is possible, by controlled nucleation and growth, to make colloids of a variety of particle sizes.

To inhibit reoxidation of the magnetic particles, they can be passivated with, for example, phosphoric acid, potassium dichromate and the like. To inhibit aggregation of the colloid, suitable surfactants can be added to stabilize the colloid. Suitable surfactants include human serum albumin (about 5 mg/ml to 50 mg/ml), polyvinyl pyrrolidone and polyethylene glycol (about 0.1 mg/ml to 2.0 mg/ml) and the like.

The biological magnetic fluids can be lyophilized for storage and transport and resuspended by adding liquid. In accordance with one preferred embodiment lyophilization is preceded by the addition of at least 10% by volume of fetal bovine serum or human serum albumin at 50 mg/ml. The powder can be reconstituted by adding water.

As discussed previously, a one step procedure for incorporating the biologically compatible polymer into the colloid can be used, or the colloid can be prepared according to the two step technique and then additional colloid formed. In the one step technique a variety of low salt biologically compatible polymers can be incorporated into the colloid since the colloid is formed with less harsh chemicals. Suitable low salt biologically compatible polymers for incorporation into the colloid with the one step technique include those set forth above for the two step technique as well as naturally occurring polymers such as polysaccharides, glycoproteins, and other proteins, such as lectins. If desired, a relatively inexpensive, insensitive polymer, such as albumin, can be attached first as in the two step technique.

Optionally, the biologically compatible polymer can be cross-linked to stabilize the surface coating. In effect, a net-like structure of biologically compatible polymer is formed which encircles the metallic particle and is therefore extremely difficult to remove. A variety of cross-linking techniques might be utilized to bind the biologically compatible polymers about the metallic nuclei without causing irreversible aggregation of the colloid. The cross-linking is accomplished for a wide variety of different biologically compatible polymers using glutaraldehyde. In addition, cyanuric chloride and water soluble carbodiimides such as 1-ethyl-3-(3-dimethylaminopropyl) carbodiimide (EDCI) may be used for this purpose.

A variety of biologically active macromolecules or affinity ligands can be attached to the colloidal particles. Generally, a biologically active macromolecule or affinity ligand is one half of an affinity system. More particularly, by affinity ligand is meant either component of a complementary binding interaction which has sufficient binding strength to allow a stable complex to form. Examples of such complementary interactions include antigen-antibody, avidin-biotin and the like.

In order to secure a variety of biologically active macromolecules to the individual dispersed phase particles to obtain biologically desirable objectives, the biologically active macromolecules may be adhered via a covalent linkage to the cross-linked biologically compatible polymer wound about the individual nuclei. A variety of methods of forming covalent linkages may be used to accomplish this function including the use of glutaraldehyde, as discussed with respect to the cross-linking step, p-benzoquinone, N,N-dicyclohexylcarbodiimide and diN-hydroxysuccinimidyl succinate. It may sometimes be desirable to use different materials as the biologically compatible polymer adhered to the cobalt particles and as the biologically active macromolecule. For example, one material may be more capable of binding to the particle and thus more suitable as the biologically compatible polymer, whereas another may have desirable biological activity and thus may be more suitable as the biologically active macromolecule.

If covalent linking to the polymer is desired, the operation may be accomplished by first attaching the colloidal particle to the linking agent or by first attaching the biologically active macromolecule to the linking agent and then attaching the colloidal particle. Better results have been obtained by activating the macromolecule with the covalent linking agent and thereafter attaching it to the colloidal particles.

The biologically active macromolecule, such as immunoglobulin, polysaccharides, lectins or other specific proteins, may be activated with a variety of covalent linking agents including p-benzoquinone. The procedure is based on the principle that p-benzoquinone in excess and at near neutral pH reacts with macromolecules by only one of its two active sites. After reaction and removal of excess p-benzoquinone, the activated macromolecule is allowed to react at a slightly alkaline pH, with a suitable secondarily added substance. Benzoquinone is known to react primarily with amino and sulfhydryl groups, but also with other reactive groups present in proteins as well as with polysaccharide moities. The use of p-benzoquinone and other covalent linking agents is described in the article by S. Avrameas, et al., "Coupling of Enzymes to Antibodies and Antigens", in Scand. J. Immunol., Vol. 8, Supp. 7, 7-23 (1978), hereby expressly incorporated by reference herein.

A preferred embodiment employs affinity ligands directly adsorbed to colloidal cobalt particles. This saves time consuming steps and aids in producing a more consistent product.

Accordingly, colloidal cobalt can be prepared as described above. The colloidal cobalt is easily prepared in solution since the cobalt particles tend to stay in suspension. This is believed to be due to the natural steric repulsion of the cobalt particles as a consequence of the particle's high negative surface charge.

Preferably, the cobalt colloid is prepared by reducing a cobalt salt solution such as cobaltous chloride with a suitable reducing agent such as sodium borohydride. The cobalt salt can be complexed initially with citrate to aid in controlling the rate of the reduction reaction. This first reduction results in the formation of minute cobalt metal nuclei which remain easily in colloidal suspension.

A second addition of cobalt-citrate complex to the suspension in dilute borohydride results in the deposition of further cobalt onto the surface of the particles. This growth results in the formation of fairly uniform spherical particles from at least about 30 nanometers in diameter and generally from about 30 nanometers in diameter to about 60 nanometers in diameter.

The cobalt colloidal suspension behaves as nearly ideal colloidal particles in the absence of a magnetic field, are attracted by a strong magnetic field, and return to a nonmagnetic colloidal suspension when the magnetic field is removed. The concentration of these colloidal spheres can be as high as $10^{10}$/ml.

At this point, various affinity ligands, such as avidin, lectins and immunoglobulins can be added to the colloidal cobalt solution and directly adsorbed onto the cobalt surface. These affinity ligand-coated cobalt particles behave much as free ligands and react with solution kinetics rather than collision kinetics.

The metallic cobalt, if left alone in an oxidizing atmosphere, dissolves over a few hours in a solution, so it is usually necessary to passivate the surface to inhibit reoxidation of the cobalt. This can be done in a variety of ways, but treatment with a phosphoric acid (in one preferred embodiment approximately 1 to 50 millimolar) and/or potassium dichromate (in one preferred embodiment approximately 1 to 50 millimolar) and/or a zinc salt (in one preferred embodiment approximately 0.1 to 10 millimolar) is effective. The excessive passivating agent is removed by dialysis, ultrafiltration, or gel filtration.

It is particularly advantageous to ultrafilter the resulting colloid using tangential flow filtration. The filtration which occurs is extremely effective because the fluid is pumped tangentially across a pressurized filtration membrane so that particles are cleared away from the membrane and blocking is lessened. This step concentrates the colloid so that it can be purified by gel filtration. The purity of the resulting colloid is critical in many applications.

To further stabilize the suspension against aggregation, other macromolecules such as human serum albumin can be added. The addition of human serum albumin will stabilize the colloid even after the addition of physiological salt solutions.

The separation of the biologically active conjugates formed from these derivatives and reagents is required. Isolated conjugates give less background and have greater specific activity than unpurified preparations. Purification of the conjugates is accomplished by the use of gel filtration columns, depending upon the size of the colloid and the molecular weight of the affinity ligand. For example, the colloidal fluid can be concentrated by Amicon tangential flow membrane filtration, and purified by gel permeation chromatography on Sepharose Cl 6B in physiological salt solution. Human serum albumin is added to the colloid peak, the fluid is sterilized by filtration and is ready for use.

The biological colloidal magnetic fluids, made in accordance with the present invention, have many potential applications. They may be used for cell separations, to target drugs, as a "target" for radiation treatment, or to block arteries. It may sometimes be advantageous to incorporate radioactive markers in the magnetic liquid. This may be done using isotopes of cobalt such as cobalt 57.

The affinity ligands of biologically active macromolecules attached to the individual colloidal magnetic particles can bind monoclonal or polyclonal antibodies which attack and adhere to specific cells of biological interest, such as cancer cells. Because of the magnetic properties of the colloid, cell separations may be accomplished. For example, cancerous bone marrow cells may be magnetically separated from normal cells.

An especially useful paramagnetic colloidal-sized particle is avidin-coated cobalt. Colloidal-sized particles of cobalt can be prepared as described previously. Avidin can be added to the colloidal cobalt, and because it is a basic protein, the avidin binds rapidly and essentially irreversibly to the surface of the particles.

The binding of avidin to the cobalt particles tends to neutralize the high negative surface charge of the cobalt particles causing the particles to aggregate. Addition of succinic anhydride decreases the positive charge on the exposed surface of the avidin bound to the particles, thus overcoming the tendency of the avidin-coated particles to aggregate.

An affinity separation system for cell mixtures using avidin-coated colloidal cobalt is provided which takes advantage of the strong binding nature of avidin and biotin. The avidin-biotin complex is essentially irreversible under most conditions. By using biotinylated monoclonal antibodies or biotinylated lectins, or other binding agents, which can selectively bind to certain cell types, avidin-coated colloidal cobalt particles can be bound to selected cells. The cobalt colloid-bound cells can then be separated from a cell mixture by exposing the mixture to a magnetic field and pulling the colloid-coated cells from the mixture.

For example, it is anticipated that a "cocktail" of monoclonal antibodies which can be used for the magnetic removal of each acute leukemia cell type could be developed. Using both biotinylated antibodies and biotinylated lectins and the like in the same cocktail, leukemia cells could be magnetically removed through the avidin-biotin interaction.

High boride containing biological magnetic liquid made by reducing a metal salt solution with a reducing agent can be used to coat selected cell populations from a mixture of cells in vitro (such as cancer cells in human bone marrow). The cancer or other cells can be selected by an appropriately specific monoclonal antibody adhered on the colloidal particles, as described above. After careful washing of the cells to remove excess (free) colloid, the cells can be dispersed evenly in a suitable medium, such as gelatin (approx. 1% concentration), to prevent sedimentation of the cells. The cells can then be exposed to a thermal neutron beam, causing the boron atoms to emit a high energy alpha particle, thereby killing the colloid coated cells, while leaving the others viable and undamaged. In this way bone marrow can be purged of cancer cells or other cells. Because of the high density of dispersed boron atoms obtainable with the present invention, the probability of achieving a boron/neutron collision would be greatly increased. Specifically, in one preferred embodiment each colloidal particle would be at least about 5% boron which means there would be in the neighborhood of 100,000 $^{10}B$ molecules per colloid particle and $5 \times 10^9$ $^{10}B$ molecules per cell (50,000 colloid particles estimated per cell).

The technology for making erythrocyte ghosts is well established (e.g. Schwoch & Passow, Molecular & Cellular Biochemistry, Vol. 2, No. 2, pp. 197-218, Dec. 15, 1973, hereby expressly incorporated herein by reference). Human albumin magnetic fluid can be used as a filler for erythrocyte ghosts, immediately after formation of the fluid, without covalently linking other functional molecules. This fluid and any additions to it, such as drugs, or radioactive markers can be incorporated into resealed erythrocyte ghosts by mixing a suspension of erythrocytes with the concentrated magnetic fluid.

The mixture is then diluted with a hypotonic magnesium/TRIS ion containing buffer to lyse the erythrocytes, which are then resealed after a few minutes by restoring the osmolarity to physiological levels with for example, sodium chloride. The cells thus encapsulate the magnetic fluid and its added substances, and can be separated and purified by a variety of methods such as density gradient centrifugation.

These magnetic erythrocyte ghosts can be used to deliver substances to medically or biologically desirable parts of the body by magnetic methods. There may be advantages to using autologous ghosts since they will not be recognized as foreign, at least initially, by the body.

The following examples are for the purpose of illustrating the invention in greater detail and shall not be construed as limiting the invention. Those skilled in the art will appreciate that the particles and magnetic fluid of the present invention can have various embodiments and uses and these are within the scope of the invention.

EXAMPLES

Example 1

Preparation of a Magnetite Cobalt Magnetic Colloid (a) Formation of Colloidal Magnetite in Protein Solution A magnetite fluid (12 nm. magnetite particles), made with an aqueous mixture of ferric chloride (40 ml., 1 molar) and ferrous chloride (10 ml., 2 molar, in HCl 2 molar), is added to ammonia solution (500 ml., 0.7 molar) at room temperature. The gelatinous precipitate is isolated from solution by centrifugation or magnetic decantation without washing with water. An alkaline ferrofluid is made by peptizing the precipitate with aqueous tetramethyl ammonium hydroxide, which as added until its concentration in the mix is at least one molar or about 180 mg./ml. The sol can be obtained only if the Fe (III) to Fe (II) weight ration is greater than two.

The magnetic fluid is slowly added to the low salt biologically compatible polymer (50 ml. of 30 mg./ml. (3%) human albumin, obtained from Baxter Travenol, Deerfield, Ill.) until the pH of the albumin is about 9.5, which is optimal for reduction by sodium borohydride. A deep brown solution with minimal aggregation results and should be left overnight at 4° C.

The solution is centrifuged at about 1000 g's for 20 minutes and filtered through a low protein binding, 0.22 micron filter. The volume is adjusted to 50 milliliters with water and the resulting material is stored at 4° C.

(b) The Growth of Cobalt/Boride on Particles and Passivation

One molar sodium borohydride ($NaBH_4$) (300 microliters) is mixed with the 50 ml. of solution produced in part (a) above at room temperature. A freshly prepared cobalt chloride solution (150 microliters) (0.5 molar $CoCl_2$ and 0.5 molar sodium citrate, in the volume ration of 3:2) is added and quickly mixed. The material is left for 5 minutes and then one molar sodium borohydride (1 ml.) is added with mixing.

Additional cobalt chloride/sodium citrate solution (2 ml.) is added and mixed as above, but this time it is allowed to sit for 15 minutes.

Potassium dichromate is added until the final concentration is 15 millimolar and zinc chloride is added to 5 millimolar, to prevent oxidization. Polyvinyl pyrrolidone (PVP) (MW 40,000) (to one milligram per milliliter) is added as a biologically safe surfactant which increases the stability of the colloid.

The colloid is ultrafiltered using a tangential flow AMICON with a 30 nanometer membrane, to obtain about 15 milliliters. The colloid is then filtered through an 0.22 micron filter and run in 10 milliliter aliquots on a gel filtration column. Suitable gel filtration beads include Sepharose CL 6B (250 milliliters), and a suitable column is 20 centimeters by 3.5 centimeters. The gel is equilibrated with PVP (one milligram per milliliter in 10 millimolars of $NaHCO_3$).

(c) Cross-linking of Albumin to Stabilize Surface Coating

The pH of the colloid is adjusted to 6.8 with phosphate buffer (to 50 millimolar final concentration in a volume of 200 milliliters). Next, 1.5% glutaraldehyde is added and the material is allowed to sit at room temperature for eighteen hours. Thereafter ultrafiltration is carried out to 10-15 milliliters using a 50 nm. membrane.

(d) Forming the Covalent Linkage for Macromolecules

Immunoglobulin (affinity purified fraction of goat anti-mouse immunoglobulins, obtained from Boehringer Mannheim Biochemicals, Indianapolis, Indiana) is activated with p-benzoquinone. To one milligram of immunoglobulin and 0.4 milliliters of 0.1 molar phosphate buffer (pH 6.0), add 0.1 milliliter p-benzoquinone and 95% ethanol (30 milligrams/milliliters). The liquid is kept in the dark for an hour. Thereafter, it is filtered through a fine column (Sephadex G-25, 0.9 centimeters by 4 centimeters) equilibrated with 0.15 molar NaCl. The first colored fraction containing the activated protein is collected in a volume of approximately 1 milliliter. One-tenth of the volume of 1 molar $NaHCO_3$ is added to the benzoquinone activated immunoglobulin and the mixture is added to the concentrated colloid in 0.1 molar $NaHCO_3/Na_2CO_3$ (pH 9.0) (1 milligram protein/5 milliliters colloid). The liquid is left for 48hours at 4° C. It is then run on a gel filtration column (Sepharose CL 6B equilibrated with phosphate buffered saline, pH 7.4) and sterile filtered using a 0.22 micron low protein binding filter.

Example 2

Alternate Formation of a Colloidal Magnetite/Cobalt Liquid

The procedure outline in paragraphs (a)-(c) of Example 1 is followed. However, the covalent linkage may be formed by the activation of the colloid with p-benzoquinone. This is done by running the colloid (10 milliliter aliquots) on a gel filtration column (Sepharose, 250 milliliters CL 6B) equilibrated with PVP, 1 milligram per milliliter, in a 10 millimolar phosphate buffer at pH 8.0. The pH is then adjusted to 6 with phosphate buffer to a final concentration of 50 millimolar. A one-fourth volume of p-benzoquinone (30 mg./ml.) in 95% ethanol is added and the mixture is kept in the dark for an hour with occasional mixing. The product is run on a column equilibrated with 10 millimolar $NaHCO_3$, and then concentrated by ultrafiltration to about 10 milliliters. The pH is adjusted to 9, so that the colloid is in 0.1 molar $NaHCO_3/Na_2Co_3$ buffer. The immunoglobulin is added to a concentration of 1 milligram per 5 milliliters of concentrated colloid. The product is left for 48 hours at 4° C. to bind. Thereafter, it is run on a gel filtration column, equilibrated with phosphate buffered saline, pH 7.4.

Example 3

Formation of a High Boride Containing Magnetic Fluid

Low salt human albumin (50 ml., 30 mg./ml.) is mixed with one molar sodium borohydride (300 microliters). Then 150 microliters of freshly prepared cobalt solution (0.5 molar cobalt chloride and 0.5 molar sodium citrate in a volume ration of 3:2) is mixed in quickly. After the liquid is allowed to sit for five minutes, one molar sodium borohydride (1 ml.) is mixed in. Then 2 milliliters of the cobalt chloride/sodium citrate mixture are added and mixed.

After the liquid has been allowed to sit for 15 minutes, potassium dichromate and zinc chloride and polyethylene glycol (20,000 MW) may be added as discussed in Example 1. Ultrafiltration and gel filtration may be accomplished also as described with respect to Example 1.

Example 4

Separation of Various Bone Marrow Cells

The colloid produced in accordance with Examples 1, 2 or 3 may be used to separate bone marrow cells into cancerous and noncancerous components or to remove graft versus host disease causing cells. This may be done by collecting bone marrow cells (1,000 cc.) from a donor by multiple aspirations from the miliac crest under general anesthesia. The cells should be kept at less than 10° C. Cells are passed through a hemonetic cell separator or gradient centrifuge to remove granulocytes and red cells. To remove graft versus host disease causing cells, the cells are incubated with mouse monoclonal antibody (CT-2) for 45 minutes at 4° C. which reacts with E-rosette receptor positive lymphocytes (T-cells). The CT-2 antibody, a pan T-cell monoclonal antibody, is described in the article by M. Trigg, R. Billing, et al., "In Vitro Treatment of Donor Bone Marrow with Anti E-rosette Antibody and Complement Prior to Transplantation," J. Cell Biochem. 7A(Supplement):57, 1983, hereby expressly incorporated by reference herein. Three washes by centrifugation of the product are undertaken with Hepes buffered Hanks balanced salt solution (HHBS) at pH 7.4 with 2% by volume fetal bovine serum (FBS).

After resuspension, the cells are incubated with affinity purified immunoglobulin fraction goat antimouse antibody bound to the magnetic fluid, made in accordance with Example 1 with 10% by volume fetal bovine albumin, for 60 minutes at 4° C. Magnetic separation is undertaken with a permanent magnet for 60 minutes at 4° C. to remove antibody colloid coated cells. Alternatively, a flow through magnetic chamber may be used with HHBS at pH 7.4 and 2% volume FBS. The chamber may be made of a stack of U-shaped cobalt-/samarium permanent magnets, developing 8,500 gauss, with concave pole faces and interior grooving of the individual magnets to focus the magnetic gradients at the passing cells. A coil or mesh of magnetic wire is contained within a siliconized glass tube held within the gap formed by the U-shaped magnets. The cells flow through the chamber by way of the siliconized tube.

The remaining cells are removed by decanting. The material is washed with Hepes buffered Hanks balanced salt solution, and filtered using a glass filter with a pore size of 40 to 80 microns followed with washing in Hanks balanced salt solution. The liquid is sampled for in vitro progenitor testing and measurement of separation efficiency. Cells are collected for intravenous infusion over thirty minutes.

Monoclonal antibody-reactive cells that escape the separation procedure are detected in a variety of ways. Immunofluorescence may be used either with a second antibody such as goat antimouse immunoglobulin, labeled with fluorescein or with a third antibody reactive with the colloid-bound antibody (rabbit antigoat immunoglobulin) labeled with fluorescein. In addition, the leukemic cells are radioactively prelabeled in culture prior to separation in mixtures with unlabeled normal bone marrow cells. Also clonogenic leukemic cells are grown in a culture after separation. Finally, a biological model using animal leukemia (rat or mouse) is used whereby even one viable remaining leukemic cell can be detected.

Antibody reactive cells have been removed to the limit of immunofluorescence (less than 1% remaining) with the recovery of antibody negative cells above 50 percent.

Example 5

An avidin-coated colloidal cobalt was prepared as follows. Freshly prepared, 0.45 micron filtered solutions of 0.5 M cobaltous chloride, 0.5 M sodium citrate, 1 M sodium borohydride, and 100 mM potassium dichromate were used. Three parts of cobalt solution was mixed with 2 parts of citrate solution to form cobalt-citrate solution. Six ml of the sodium borohydride solution were added to 100 ml of water, and after mixing, 1 ml of the cobalt citrate solution was added while rapidly swirling the container. Almost immediately, a brown color appeared due to the formation of colloidal cobalt particles.

After one minute a second addition of a ml of the cobalt citrate solution was performed with rapid swirling. After two minutes the solution was made basic by the addition of 1 ml of 1 N sodium hydroxide. After mixing, a solution containing 5 mg of purified avidin was added, followed by the addition of a solution containing 20 ug of succinic anydride in N,N'-dimethylformamide.

Five ml of a 25% solution of human serum albumin is added, followed by 10 ml of 100 mM potassium dichromate.

The colloidal fluid was then concentrated to about 40 $OD_{400}$ units per ml in a tangential flow Amicon concentrator, and filtered through a 0.45 micron filter. The colloid was separated from unbound reagents by gel filtration in a column of Sepharose-6B in phosphate buffered saline (PBS) at pH 7.4. The dark peak of colloid was collected and 1/10 volume of a solution of 25% human serum albumin was added. The colloid was sterilized by filtration.

Example 6

Using avidin-coated colloidal cobalt prepared according to Example 5, removal of T-lymphocytes was accomplished generally as follows.

A mononuclear cell fraction of bone marrow cells was incubated with a pool of monoclonal antibodies, OKT3 +OKT4+OKT8+OKT11, for 30 minutes a 4° in PBS containing 2% fetal bovine serum (PBS-FBS). The cells were washed by centrifugation in PBS-FBS twice.

The cells were next incubated with a biotin-labeled affinity purified IgG fraction of goat-antimouse immunoglobulin (G-GAM) for 30 minutes at 4° in PBS-FBS and washed as above.

The cells were then incubated with the avidin-cobalt colloid in PBS-HSA for 30 minutes at 4° and washed once PBS-FBS and passed through a high-magnetic gradient separation column. The magnetic cells were restrained, and the unreactive cells passed through the column.

The results are depicted in the following table:

| Expt | Rgt | % Positive | % Pos. Cell[a] Removal | % Neg. Cell[b] Recovery | % T-Cell[c] Removal |
|---|---|---|---|---|---|
| 1 | OKT-C | 61.9 | 99.7 | 93.4 | 99.0 |
| 2 | OKT-C | 24.6 | 94.2 | 40.7 | 99.0 |
| 3 | OKT-C | 30.3 | 99 | 32.0 | 99.8 |
| 4 | OKT-C | 37.5 | 97.7 | 63.0 | 99.1 |
| 5 | OKT-C | 38.6 | 99 | 61.6 | 99.2 |
| 6 | OKT-C | 46.1 | 99 | 72.9 | 99.2 |
| 6 expts | | | 98.1 | 65.6 | 99.2 |

[a] $100 - \frac{(\% \text{ pos. cells after-control})}{(\% \text{ pos. cells before-control})} \times \text{total cell recovery}$

[b] The % negative cell recovery was calculated as follows:
% neg. cell rec. $= \frac{\text{Total recovery} - (\% \text{ pos. cells after-control})}{100 - (\% \text{ pos. cells before-control})}$ Where the control contains FITC-A preincubated with biotin prior to staining and total recovery =
$\frac{\text{Cell \# after separation}}{\text{Cell \# before separation}}$

[c] analysis by limiting dilution T cell culture technique

While the present invention has been described with respect to a limited number of embodiments, those skilled in the art will appreciate a number of modifications and variations. It is intended within the appended claims to cover all such modifications and variations as come within the true spirit and scope of the claims.

What is claimed is:

1. A colloidal biological magnetic fluid comprising a colloidal dispersed phase further comprising colloidal-sized substantially spherical paramagnetic cobalt particles coated with affinity ligands directly adsorbed to the particle surface, said colloidal dispersed phase distributed through an aqueous dispersion medium.

2. The biological magnetic fluid of claim 1 wherein said affinity ligands are avidin, lectins or immunoglobulins.

3. The biological magnetic fluid of claim 1 wherein said colloidal dispersed phase is passivated to inhibit reoxidation of said cobalt particles.

4. The biological magnetic fluid of claim 3 wherein said colloidal dispersed phase is passivated with dichromate.

5. The biological magnetic fluid of claim 1 wherein said colloidal dispersed phase is stabilized.

6. The biological magnetic fluid of claim 5 wherein said colloidal dispersed phase is stabilized with human serum albumin.

7. A method of making a colloidal biological magnetic fluid comprising:
(a) reducing a complexed aqueous solution of a cobalt salt with a reducing agent to form an aqueous colloidal suspension of cobalt;
(b) adding an aqueous solution of affinity ligands;
(c) stabilizing said colloidal suspension; and
(d) passivating said colloidal suspension.

8. The method of claim 7 wherein said reduction of complexed aqueous solution of cobalt salt is accomplished in two stages comprising:
(a) reducing a first portion of said complexed aqueous solution of cobalt salt with a reducing agent to form an initial aqueous colloidal suspension; then
(b) reducing the remainder of said complexed aqueous solution of cobalt salt with said reducing agent.

9. The method of claim 7 further comprising ultrafiltering said stabilized and passivated colloidal magnetic fluid to concentrate said colloidal suspension.

10. The method of claim 9 further comprising separating unbound affinity ligands by gel filtration.

11. The method of claim 10 further comprising sterilizing said colloidal suspension by filtration.

12. The method of claim 7 further comprising adding human serum albumin and then lyophilizing the magnetic liquid.

13. A fluid, comprising an aqueous colloidal suspension of substantially spherical paramagnetic cobalt particles coated with affinity ligands adsorbed directly to the surface of the particle.

14. The fluid of claim 13 wherein the affinity ligands are avidin, lectins or immunoglobulins.

15. The fluid of claim 13 wherein the cobalt particles range in size from at least about 30 nanometers in diameter.

* * * * *